(12) United States Patent
Olson

(10) Patent No.: US 8,154,416 B1
(45) Date of Patent: Apr. 10, 2012

(54) UNDERSEAT WHEEL CHAIR ALARM

(75) Inventor: Richard T. Olson, Cedar Rapids, IA (US)

(73) Assignee: Professional Security Corporation, Cedar Rapids, IA (US)

( * ) Notice: Subject to any disclaimer, the term of this patent is extended or adjusted under 35 U.S.C. 154(b) by 559 days.

(21) Appl. No.: 12/487,820

(22) Filed: Jun. 19, 2009

(51) Int. Cl.
- *G08B 21/00* (2006.01)
- *G08B 13/14* (2006.01)
- *A47B 97/00* (2006.01)

(52) U.S. Cl. ............ 340/667; 340/666; 340/573.1; 340/686.4; 280/250.1; 280/304.1; 297/463.1; 297/DIG. 4; 180/273; 200/85 A

(58) Field of Classification Search .............. 340/667, 340/666; 200/85 A
See application file for complete search history.

(56) References Cited

U.S. PATENT DOCUMENTS

| | | | |
|---|---|---|---|
| 3,903,513 A | 9/1975 | Green et al. | |
| 6,288,649 B1 * | 9/2001 | Wolfe | 340/667 |
| 6,371,503 B2 * | 4/2002 | Ritchie et al. | 280/304.1 |
| 6,544,200 B1 * | 4/2003 | Smith et al. | 600/595 |
| 6,847,301 B1 | 1/2005 | Olson | |
| 6,963,286 B2 | 11/2005 | Marquis et al. | |
| 7,061,389 B2 * | 6/2006 | Senoo | 340/667 |
| 7,331,071 B1 | 2/2008 | Cherubini et al. | |

\* cited by examiner

*Primary Examiner* — Donnie Crosland

(74) *Attorney, Agent, or Firm* — Jason R. Sytsma; Shuttleworth & Ingersoll, PLC

(57) ABSTRACT

In accordance with one aspect of the present invention, an alarm assembly for a wheel chair is disclosed. A pair of mounting brackets is combined to the frame underneath the seat of the wheel chair. A removable and extendable switch-bar selectively combines to the mounting brackets. The switch-bar is adjustable in length to accommodate chairs of various widths and selectively positionable on the mounting brackets to change the distance between the seat and switch. The switch on the switch-bar senses the presence of a patient and in response to the absence of a patient communicates an alarm signal to the alarm.

20 Claims, 5 Drawing Sheets

UNDERSEAT WHEEL CHAIR ALARM

TECHNICAL FIELD

The disclosure relates to a wheel chair alarm system, specifically a removable and adjustable alarm system.

BACKGROUND INFORMATION

Although wheel chair alarms exist, the construction of these alarm systems is not well suited to the practical use of wheel chairs. Specifically, removing the prior art alarm systems for washing the chairs takes an inordinate amount of time. Alarm systems having electrical circuitry need to be removed when cleaning the chairs, otherwise damage to the alarm system may result. Often alarm systems are combined to the chair in such a manner that the seat needs to be removed before removing the alarm system.

Accordingly, there is a need for an improved wheel chair alarm system that is easily removable.

SUMMARY

In accordance with one aspect of the present invention, an alarm assembly for a wheel chair is disclosed. A pair of mounting brackets is combined to the frame underneath the seat of the wheel chair. A removable and extendable switch-bar selectively combines to the mounting brackets. The switch-bar is adjustable in length to accommodate chairs of various widths and selectively positionable on the mounting brackets to change the distance between the seat and switch. The switch on the switch-bar senses the presence of a patient and in response to the absence of a patient communicates an alarm signal to the alarm.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1:
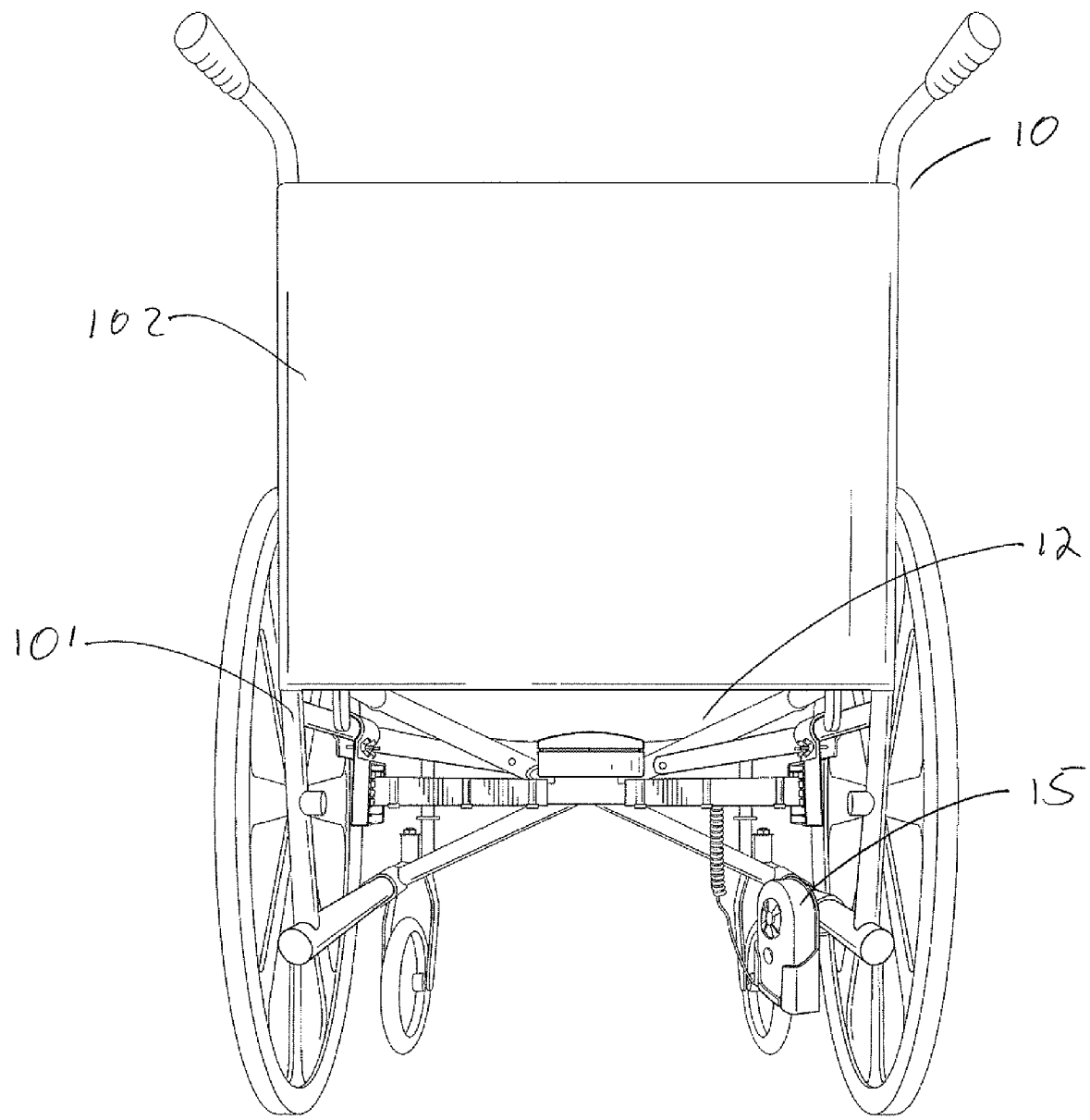
FIG. 1 is a view of the wheel chair alarm system combined with the wheel chair.

FIG. 1 illustrates a wheelchair, generally shown as 10. The alarm system, generally indicated as 12 and described in further detail below, may be used on any type of wheelchair, and thus the one depicted herein is provided solely for illustrative purposes and is not intended to be limiting. The alarm system may be installed in the wheelchair 10 as original equipment (i.e. the wheelchair manufacture may install it as part of assembly), or it may be a retrofit system designed to be installed to existing wheelchairs 10 in the field, or used by those purchasing wheelchairs for purposes of retrofitting prior to usage.

Generally, wheelchairs 10 are measured according to the width of the seat 102. A standard wheel chair 10 has a seat width of 18 inches. Generally, the overall width of the wheel chair 10 with an 18 inch seat 102 has a width of 24.5 to 26.5 inches. Wheel chair 10 seat widths may be greater than 18 inches to accommodate larger patients, including seats 102 up to 24 inches. A 24 inch seat 102 may have an overall width of 32 inches. Accordingly, the alarm system 12 is designed to accommodate wheel chair widths of different sizes.

Figure 2:
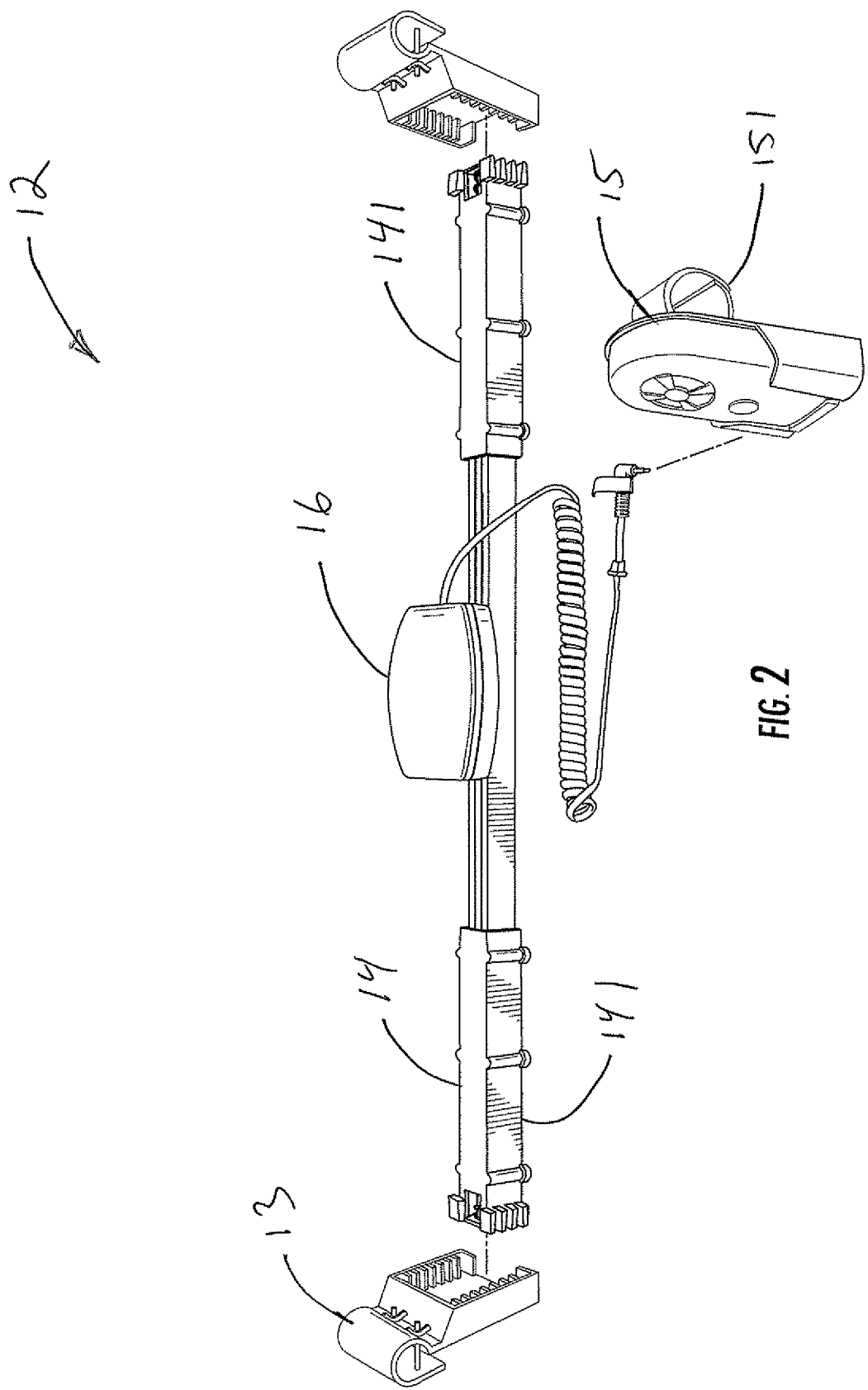
FIG. 2 is a view of the wheel chair alarm system.
Figure 3:
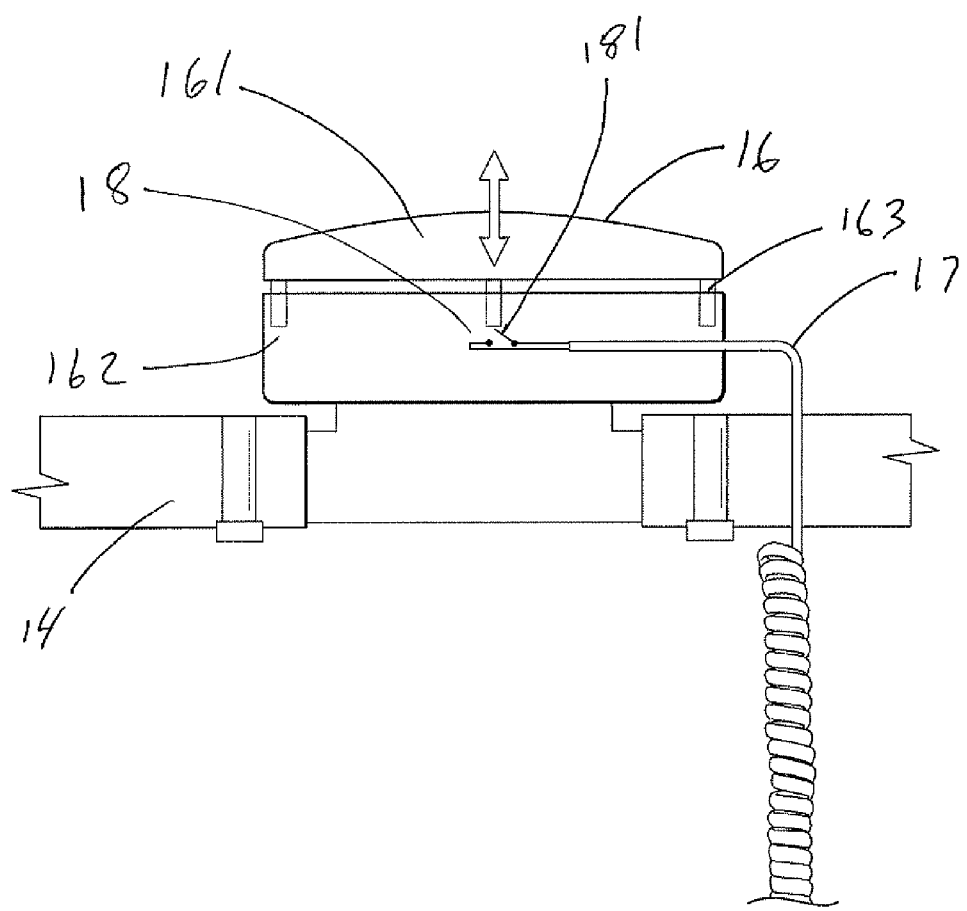
FIG. 3 is an enlarged perspective view of the switch-housing of the alarm system.

Referring to FIGS. 2-3, the alarm system 12 comprises an alarm device 15, illustrated as an audible horn by way of example, operable to emit a warning signal. The alarm device 15 may be mounted anywhere on the wheelchair 1, including on the frame 101 or on the back of the seat 102. In the illustrated embodiment, the alarm is mounted on the frame 101 underneath the seat 102 by a clip 151 that wraps around the frame 101. The warning signal emitted by the alarm 15 may be of any type, such as a visual signal (e.g., a warning light), an audible signal (e.g., a horn or beeping device), or a remote signal (e.g., a signal transmitted to a nursing station for alerting personnel). Generally, the alarm device 15 may be of any suitable type and the one illustrated herein is not intended to be limiting.

An underseat alarm switch-housing 16 having an internal switch 18 is in communication with the alarm device 15. The housing 16 has a top portion 161 and a bottom portion 162 combined by one or more springs 163. In the normal position the springs 163 hold the top portion 161 of the housing 16 up and the switch 18 disengaged; however, when pressure is applied to the top portion 161 the top portion moves downward engaging the switch 18, signaling the alarm that a patient is on the seat 10.

In the illustrated embodiment, cable 17 provides communication between the switch-housing 16 and the alarm device 15; however, communication could be wireless by any known or future means of wireless communication (not shown). In such a case, the switch-housing 16 would have transmitter circuitry for communicating an alarm signal and the alarm device 15 would have receiver circuitry receiving the alarm signal. Further, any type of switch 18 may be used and one skilled in the art would recognize that the alarm device 15 could be programmed to cooperate with either a normally open or normally closed switch.

Figure 5:
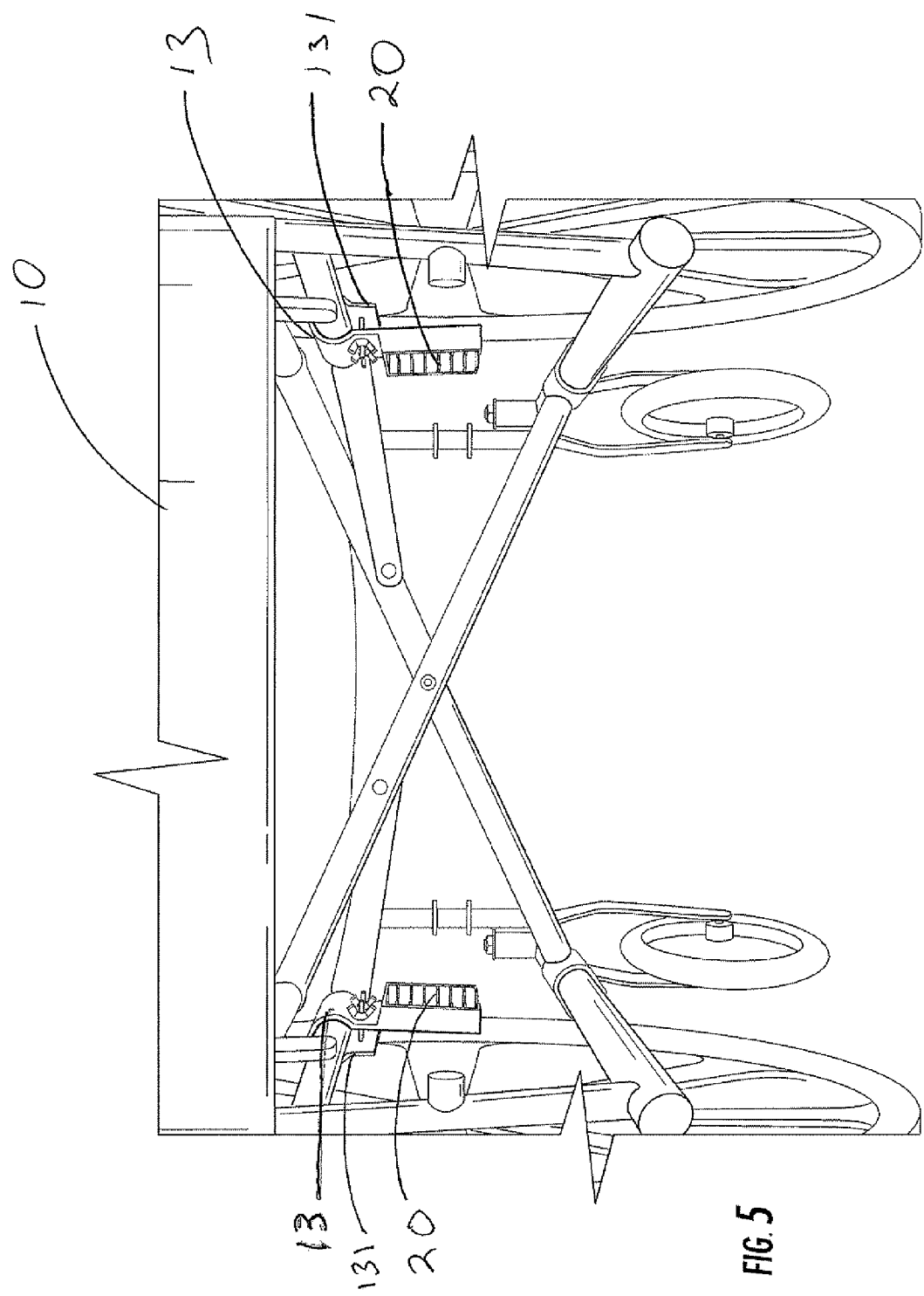
FIG. 5 is an embodiment of the wheel chair alarm system removed from the wheel chair leaving only the mounting brackets combined with the wheel chair.

The underseat alarm switch-housing 16 is connected to the wheelchair 10 by a removable and extendable switch-bar 14. The switch-bar 14 has telescoping ends 141 for allowing the switch-bar 14 to expand and retract to fit various sizes of wheel chairs 10. The switch-bar 14 is also readily removable. One or both ends 141 are retracted which allows the switch-bar 14 to be removed from the mounting brackets 13. As illustrated in FIG. 5, the switch-bar 14 has been removed and the wheelchair 10 is free to be folded for storing, transporting, or cleaning.

The illustrated embodiment discloses an alarm system 12 that is readily removable leaving the mounting brackets 13 combined with the wheel chair 10; therefore an embodiment provides brackets 13 constructed of rust proof material, such as plastic. Additionally, it may be advantageous to construct the switch-bar 14 and switch-housing 16 from rust proof material.

In the illustrated embodiment, the switch-bar 14 is combined with the wheelchair 10 by the mounting brackets 13. The mounting brackets 13 are uniquely designed to allow the switch-bar 14 to be readily and easily removed from the wheelchair 10 and also allow the distance of the switch-bar 14 from the bottom of the seat 102 and the top of the switch-housing 16 to be adjusted. Since, wheelchair seats 102 are often made of fabric, heavier patients cause the seat 102 to flex downward more. Having a switch-bar 14 that is readily adjustable in height makes it easy for the nurse to lower the switch-bar 14 to accommodate heavier patients.

Figure 4:
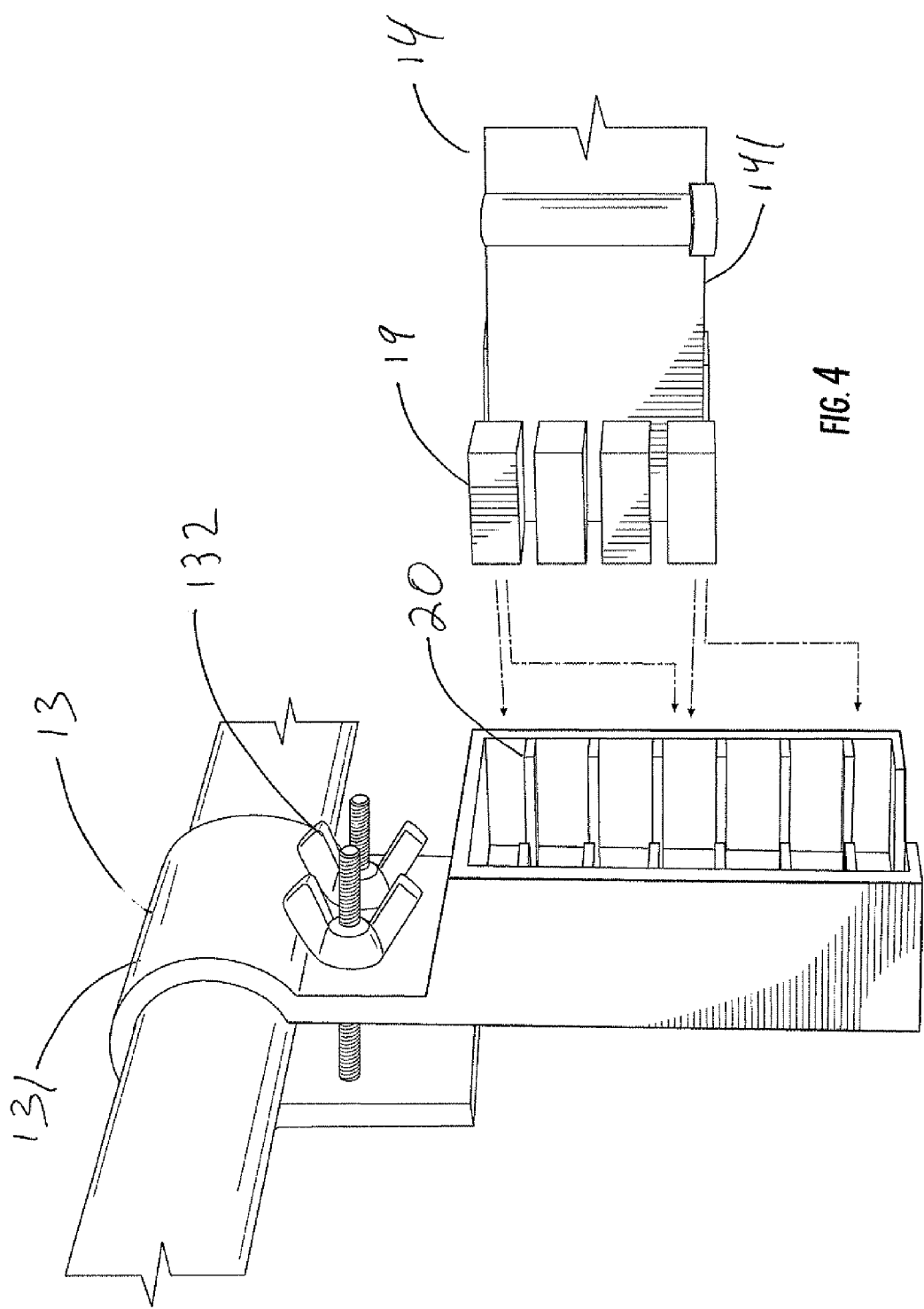
FIG. 4 is an enlarged perspective view of the mounting brackets and the switch-bar's fingers of the alarm system.

FIG. 4 illustrates an embodiment of the mounting bracket 13. The mounting bracket 13 is combined with the frame 101 by a clip 131 and tightened by wing-nuts 132. The mounting bracket has a plurality of receptacles 20 for receiving a finger 19 on end of the switch-bar 14. In an embodiment, several fingers 19 are vertically aligned to provide more contact surface for holding the switch-bar 14 in a more sturdy position. The fingers 19 may be positioned in a plurality of positions in the receptacle 20 for adjusting the height of the switch-bar 14.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

I claim:

1. An alarm assembly for a wheel chair, the alarm assembly comprising:
   a pair of mounting brackets adapted to combine with the wheel chair;
   a removable switch-bar having a switch disposed thereon, said switch-bar adapted to selectively engage said mounting brackets in a plurality of positions thereby selectively positioning said switch relative to the seat; and
   an alarm device in communication with said switch.

2. The adjustable wheel chair alarm assembly of claim 1, wherein said mounting brackets have a plurality of vertically arranged receptacles adapted to receive said switch-bar in a plurality of positions.

3. The adjustable wheel chair alarm assembly of claim 1, wherein said switch-bar has a plurality of fingers at the end of said switch-bar for selectively engaging said mounting bracket receptacles.

4. The adjustable wheel chair alarm assembly of claim 1, wherein said switch-bar length is adjustable.

5. The adjustable wheel chair alarm assembly of claim 1, wherein said switch-bar has telescoping ends to selectively extend the length of said switch-bar.

6. The adjustable wheel chair alarm assembly of claim 1, wherein said switch-bar length is adjustable to fit the wheel chairs having seats 18 inches to 24 inches in width.

7. The adjustable wheel chair alarm assembly of claim 1, wherein said switch is contained in a switch-housing.

8. The adjustable wheel chair alarm assembly of claim 1, wherein said housing comprises an upper portion and a lower portion interposed with at least one spring.

9. The adjustable wheel chair alarm assembly of claim 1, wherein said mounting brackets are made of a rust proof material.

10. An alarm assembly for a wheel chair, the alarm assembly comprising:
    a pair of mounting brackets adapted to combine with the wheel chair;
    a switch-bar having a switch contained in a spring loaded switch housing disposed thereon, said switch-bar adapted to selectively engage said mounting brackets in a plurality of positions thereby selectively positioning said switch relative to the seat; and
    an alarm device in communication with said switch.

11. The alarm assembly of claim 10, wherein said alarm device produces an audible alarm.

12. The alarm assembly of claim 10, wherein said alarm device produces an alarm signal that is transmitted to a remote station.

13. The alarm assembly of claim 10, wherein said mounting brackets have a plurality of vertically arranged receptacles adapted to receive said switch-bar in a plurality of positions.

14. The alarm assembly of claim 10, wherein said switch-bar has a plurality of fingers at the end of said switch-bar for selectively engaging said mounting bracket receptacles.

15. The adjustable wheel chair alarm assembly of claim 10, wherein said switch-bar length is adjustable.

16. The adjustable wheel chair alarm assembly of claim 10, wherein said switch-bar has telescoping ends to selectively extend the length of said switch-bar.

17. An alarm assembly for a wheel chair, the alarm assembly comprising:
    a pair of mounting brackets adapted to combine with the wheel chair;
    a removable switch-bar having a switch contained in a spring loaded switch housing disposed thereon, said switch-bar adapted to selectively engage said mounting brackets in a plurality of positions thereby selectively positioning said switch relative to the seat, said switch-bar further adapted to selectively extend in length to accommodate wheel chairs of various sizes; and
    an alarm device in communication with said switch.

18. The alarm assembly of claim 17, wherein said mounting brackets have a plurality of vertically arranged receptacles adapted to receive said switch-bar in a plurality of positions.

19. The alarm assembly of claim 17, wherein said switch-bar has a plurality of fingers at the end of said switch-bar for selectively engaging said mounting bracket receptacles.

20. The adjustable wheel chair alarm assembly of claim 19, wherein said switch-bar has telescoping ends to selectively extend the length of said switch-bar.

\* \* \* \* \*